United States Patent [19]

Burgoyne, Jr. et al.

[11] Patent Number: 4,994,105
[45] Date of Patent: Feb. 19, 1991

[54] N,N'-BIS(ALKOXYALKYL)-N,N'-(2-HALOACETYL)PHENYLENEDIAMINES

[75] Inventors: William. F. Burgoyne, Jr., Emmaus, Pa.; Dale D. Dixon, Venice, Fla.

[73] Assignee: Air Products and Chemicals, Inc., Allentown, Pa.

[21] Appl. No.: 364,933

[22] Filed: Jun. 12, 1989

[51] Int. Cl.$^5$ .................... A01N 31/18; C07C 307/56
[52] U.S. Cl. ..................................... 71/118; 364/253
[58] Field of Search ..................... 564/209; 621/118

[56] References Cited

U.S. PATENT DOCUMENTS

| | | | |
|---|---|---|---|
| 3,557,211 | 1/1971 | Rumanowski | 564/155 X |
| 3,991,581 | 3/1975 | Teach | 564/155 X |
| 4,028,093 | 6/1977 | Teach | 71/118 |
| 4,322,553 | 3/1982 | Chupp | 564/209 |
| 4,324,580 | 4/1982 | Vogel et al. | 71/118 |

Primary Examiner—Robert V. Hines
Attorney, Agent, or Firm—Keith D. Gourley; James C. Simmons; William F. Marsh

[57] ABSTRACT

Compounds corresponding to the formula:

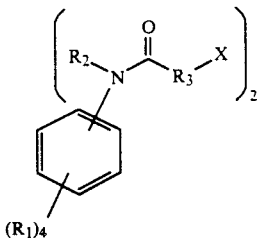

wherein:
each $R_1$ is independently selected from H, a straight chain or branched $C_1$–$C_{10}$ alkyl, $C_1$–$C_8$ alkoxy, $C_2$–$C_{10}$ alkenyl or $C_3$–$C_7$ cycloalkenyl group;
each $R_2$ is independently selected from $$-CH_2(CH_2)_mO(CH_2)_nCH_3 \text{ and}$$

$$-\underset{\underset{CH_3}{|}}{C}H(CH_2)_mO(CH_2)_nCH_3$$

wherein m and n are independently selected integers from 0 to 4, inclusive;
each $R_3$ is independently selected from a straight chain or branched $C_1$–$C_{10}$ alkylene; and
each X is independently selected from F, Cl, Br or I.

These compounds demonstrate utility as herbicidal and fungicidal compositions for controlling weeds and grasses in agricultrual crops.

22 Claims, No Drawings

N,N'-BIS(ALKOXYALKYL)-N,N'-(2-HALOACETYL)PHENYLENEDIAMINES

TECHNICAL FIELD

The present invention relates to N,N'-bis(alkoxyalkyl)-N,N'-bis(2-haloacetyl)phenyldiamine compounds which demonstrate utility as herbicidal/fungicidal compositions for controlling weeds and grasses in agricultural crops.

BACKGROUND OF THE INVENTION

Herbicides and fungicides play a significant role in ensuring that an adequate food supply at reasonable prices reaches the ever-increasing world population. The high-yield cultivation of rice is essential to ensure an adequate food supply in many countries. Itinerant weeds and grasses in the presence of rice, also a grass, dramatically reduce crop yield. Consequently, considerable research s being conducted to control, if not eliminate, such undesirable weeds and grasses. Herbicides and fungicides useful in the cultivation of rice must have selective biological activity wherein the un-Wanted grasses and weeds are caused to wither and die while leaving the rice unharmed by the treatment.

Certain chloroacetanilides have been identified as herbicides for the pre-emergent treatment and control of weeds and grasses in rice crops. Representative chloroacetanilides are disclosed in U.S. Pat. No. 4,322,553 which relates to a process for preparing N-(halomethyl)acrylamides as represented by the formula:

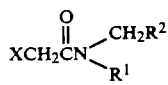

wherein X includes hydrogen, the halogens, a $C_1$-$C_6$ alkyl or haloalkyl radical, a $C_3$-$C_7$ cycloalkyl radical, a phenyl or benzyl radical; R includes a $C_{1-20}$ alkyl radical and a phenyl radical, and $R^2$ is a chloro or bromo atom.

U.S. Pat. No. 4,028,093 teaches meta-bis-anilide derivatives which demonstrate utility as herbicides. The bis-anilide derivatives are represented by the formula:

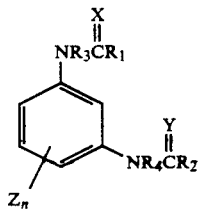

in which $R_1$ and $R_2$ are independently selected from hydrogen alkyl, alkoxyalkyl, cycloalkyl, pinonyl, ethylcycloalkyl, lower alkenyl, halogenated lower alkyl, benzyl, ethylphenyl, 2,4-dichlorophenoxymethylene, styryl, furyl, phenyl or substituted phenyl in which the substituents are nitro, halogen, methyl or methoxy; $R_3$ and $R_4$ are independently selected from hydrogen, or lower alkyl; X and Y are independently selected from oxygen or sulfur; and Z s a halogen, nitro, amino, lower alkyl, lower alkoxy or trifluoromethyl and n is an integer having a value from 0 to 4. The compounds are stated to be effective herbicides for controlling grasses and broadleaf plants demonstrating both pre-emergent and post-emergent activity.

U.S. Pat. No. 4,324,580 teaches 2,6-diethyl-N-(1'-methoxyprop-2'-yl)-[N]-chloroacetanilide as a plant growth regulating and herbicidal agent having improved stability in the soil.

SUMMARY OF THE INVENTION

The present invention provides compounds represented by the formula:

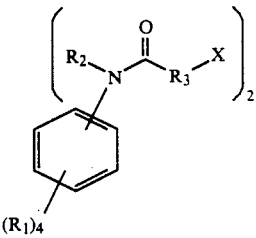

wherein:
each $R_1$ is independently selected from H, a straight chain or branched $C_1$-$C_{10}$ alkyl, $C_1$-$C_8$ alkoxy, $C_2$-$C_{10}$ alkenyl or $C_3$-$C_7$ cycloalkenyl group;
each $R_2$ is independently selected from $$-CH_2(CH_2)_mO(CH_2)_nCH_3 \text{ and}$$

$$-\underset{\underset{CH_3}{|}}{CH}(CH_2)_mO(CH_2)_nCH_3$$

wherein m and n are independently selected integers from 0 to 4, inclusive;
each $R_3$ is independently selected from a straight chain or branched $C_1$-$C_{10}$ alkylene; and
each X is independently selected from F, Cl, Br, or I.

These compounds demonstrate utility as herbicides and fungicides in the treatment and control of grasses and weeds in agricultural crops such as rice.

DETAILED DESCRIPTION OF THE INVENTION

This invention relates to novel N,N'-bis(alkoxyalkyl)-N,N'-bis(2-haloacetyl)phenylenediamine compounds which are useful as herbicides and fungicides. The novel compounds of the present invention are represented by the formula:

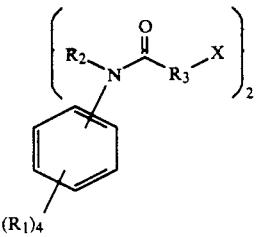

wherein:
each $R_1$ is independently selected from H, a straight chain or branched $C_1$-$C_{10}$ alkyl, $C_1$-$C_8$ alkoxy, $C_2$-$C_{10}$ alkenyl or $C_3$-$C_7$ cycloalkenyl group;
each $R_2$ is independently selected from $$-CH_2(CH_2)_mO(CH_2)_nCH_3 \text{ and}$$

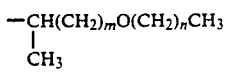

wherein m and n are independently selected integers from 0 to 4, inclusive;
each $R_3$ is independently selected from a straight chain or branched $C_1$–$C_{10}$ alkylene; and
each X is independently selected from F, Cl, Br or I.

Unless otherwise indicated, the terms "alkyl" and "alkoxy" are meant to include primary, secondary and tertiary groups. For example, the term alkyl refers to those substituents having from 1 to 10 carbon atoms, inclusive, in both straight chain and branched chain configurations. Representative alkyl groups include methyl, ethyl, propyl, isopropyl, butyl, isobutyl, tert-butyl and the like. Preferred alkyl groups are branched chain alkyl groups having from 4 to 8 carbons atoms. The tert-butyl group is particularly preferred when the contemplated substituent represented by $R_1$ is an alkyl group.

The term alkoxy refers to those hydroxy-containing substituents having from 1 to 10 carbon atoms, inclusive, in both straight chain and branched chain configurations. Representative alkoxy groups include methoxy, ethoxy, the isomeric configurations of butoxy and other alkoxy groups having from 5 to 10 carbon atoms.

When reference is made to the terms alkenyl and cycloalkenyl, the invention contemplates substituents having at least one unsaturated bond although dienes and trienes, whether Conjugated Or unconjugated are also contemplated. Representative alkenyl groups include straight chain and branched chain alkenyls such as ethenyl, propenyl, isopropenyl and the like while cycloalkenyl grOups include non-aromatic cyclic substituents, whether branched or not, containing from 3 to 7 carbon atoms. Representative of such cyclic substituents are cyclobutenyl, cyclopentenyl, cyclohexenyl and their alkyl substituted analogs.

The substituents designated as X are independently selected from the halogens including a fluorine atom (F), chlorine atom (Cl), bromine atom (Br) or iodine atom (I).

Preferred are compounds represented by the formula:

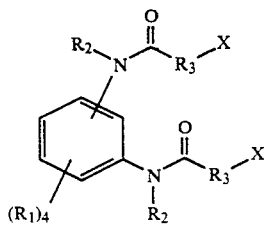

wherein:
each $R_1$ is independently selected from H, a straight chain or branched $C_1$–$C_{10}$ alkyl, $C_1$–$C_8$ alkoxy, $C_2$–$C_{10}$ alkenyl or $C_3$–$C_7$ cycloalkenyl group;
each $R_2$ is independently selected from —CH$_2$(CH$_2$)$_m$O(CH$_2$)$_n$CH$_3$ and

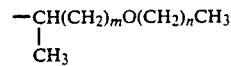

wherein m and n are independently selected integers from 0 to 4, inclusive;
each $R_3$ is independently selected from a straight chain or branched $C_1$–$C_{10}$ alkylene; and
each X is independently selected from F, Cl, Br, or I.

The compounds of this invention are prepared by reacting an aromatic diamine with an alkoxyalkyl chloride under basic conditions. The resulting intermediate is reacted with a haloacetylhalide such as chloroacetyl chloride under conditions sufficient to effect a Schotten-Baumann type reaction. Other synthetiC routes to the compounds of this invention will be apparent to those of ordinary skill in the art.

These compounds differ greatly from known chloroacetanilide-type compounds in that the subject compounds are phenylenediamines possessing a chloroacetyl and an alkoxyalkyl groups on each of the amino groups. The two substituted amino groups preferably reside in ring positions meta to each other.

The compounds of the present invention may be utilized as herbicides and fungicides by diluting the desired biologically active compound in a suitable solvent carrier such as water. Additives such as emulsifiers and surface-active agents may be added to enhance metabolic activity by influencing penetration, retention and surface tension. These herbicidal/fungicidal compositions may be applied by methods known in the art before the crop or weeds emerge from the ground (pre-emergence) or following emergence of the crop or weeds through the soil surface (post-emergence). An effective amount of a N,N'-bis(alkoxyalkyl)-N,N'-bis(2-haloacetyl)phenylenediamine compound is utilized, i.e., that amount which provides the highest degree of herbicidal and/or fungicidal activity without harming the food crop. Such effective amounts are readily determined by those skilled in the art.

Particularly preferred compounds of the present invention are represented by the formula:

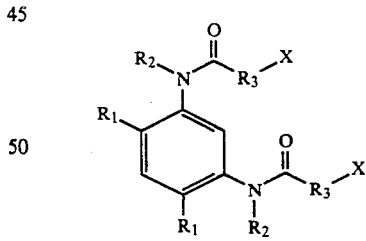

wherein:
each $R_1$ is independently selected from H or a straight chain or branched $C_1$–$C_{10}$ alkyl, $C_1$–$C_8$ alkoxy, $C_2$–$C_{10}$ alkenyl or $C_3$–$C_7$ cycloalkenyl group;
each $R_2$ is independently selected from —CH$_2$(CH$_2$)$_m$O(CH$_2$)$_n$CH$_3$ and

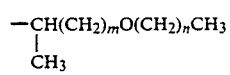

wherein m and n are independently selected integers from 0 to 4, inclusive;

each $R_3$ is independently selected from a straight chain or branched $C_1$-$C_{10}$ alkylene; and
each X is Cl.

A particular N,N'-bis(alkoxyalkyl)-N,N'-bis(2-haloacetyl)-phenylenediamine compound which demonstrates both fungicidal and herbicidal activity in the pre-emergent treatment of grasses and weeds in rice crops is represented by the formula

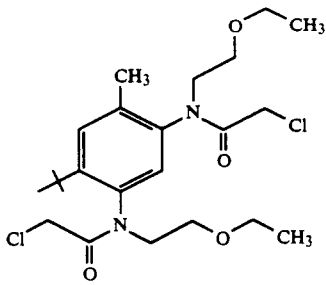

Compounds of the present invention are prepared in accordance with the following illustrative examples.

EXAMPLE 1

PREPARATION OF N,N'-BIS(2-ETHOXYETHYL)-N,N'-BIS(2-CHLOROACETYL)-4-TERT-BUTYL-6-METHYL-1,3-PHENYLENEDIAMINE

A mixture of 10.00 g (0.05609 mol) of 5-tert-butyl-2,4-diaminotoluene, 24.36 g (0.2244 mol) of 2-chloroethyl ethyl ether, and 22.70 g (0.2244 mol) of triethylamine were combined and heated to 100° C. in a sealed, 100 ml flask with magnetic stirring for 66 hours. The reaction product was cooled then filtered to remove triethylammonium chloride. After washing the ammonium salt with ca. 35 mol of ethyl acetate, the product filtrate and the ethyl acetate washing were combined and the volatiles were removed by evaporation under reduced pressure. The residual product (17.35g) had the following composition:

| Component | wt % |
|---|---|
| 5-tert-butyl-2,4-diaminotoluene | trace |
| 2-(2-ethoxyethyl)amino-4-amino-5-tert-butyltoluene | 17.90 |
| 2-amino-4-(2-ethoxyethyl)amino-5-tert-butyltoluene | 13.79 |
| 2,4-bis[(2-ethoxyethyl)amino]-5-tert-butyltoluene | 57.23 |
| other N-ethoxyethylates | 11.08 |

The entire ethoxyethylated diamine product was dissolved in 500 ml of methylene chloride. This solution was then added to 40.00 g (0.476 mol) of sodium bicarbonate in 60 ml of water. With vigorous stirring, 43.58 g (0.386 mol) of 2-chloroacetyl chloride was added proportionately over a 0.5 hr period. After the addition, the mixture was stirred an additional 3 hr. A 200 ml portion of water was added to the mixture and the layers were separated. The organic layer was dried over anhydrous magnesium sulfate then the volatiles were evaporated under reduced pressure. The residual product mixture contained 56.28 wt % of the dichloroacylated product. After purifying the product via column chromatography (silica gel; 230-400 mesh, grade 60, developed with 10:90 (V/V) ethyl acetate: methylene chloride), 10.35 g of N,N'-bis(2-ethoxyethyl)-N,N'-bis(2-chloroacetyl)-4-tert-butyl-6-methyl-1,3phenylenediamine was obtained with a purity>97.2%. This material was a dark oil which gave $^1H$ and $^{13}C$ NMR and mass spectral analyses consistent with the assigned structure.

EXAMPLE 2

EVALUATION OF HERBICIDAL/FUNGICIDAL ACTIVITY

The compound prepared in Example 1 and six other structurally similar compounds were evaluated for herbicidal and fungicidal activity by a leading manufacturer of herbicides utilizing methods well known in the art. In particular, the comparative compounds are tert-butyl-substituted phenylenediamines wherein each of the amino groups do not possess both chloroacetyl and alkoxyalkyl functionality. The following is a summary of results:

| Compound | Run | Herbicide Activity | Fungicide Activity |
|---|---|---|---|
| 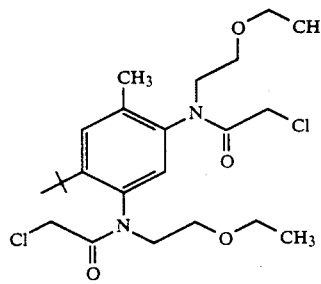<br>(prepared in Example 1) | 1 | Active | Active |

| Compound | Run | Herbicide Activity | Fungicide Activity |
|---|---|---|---|
| [structure] | 2 | Inactive | Inactive |
| [structure] | 3 | Inactive | Inactive |
| [structure] | 4 | Inactive | Inactive |
| [structure] | 5 | Inactive | Inactive |
| [structure] | 6 | Inactive | Inactive |
| [structure] | 7 | Inactive | Inactive |

The results demonstrate that Run 1 of the present invention which possesses both a chloroacetyl group and an alkoxyalkyl group on each of the amino groups shows both herbicidal and fungicidal activity. In contrast, Runs 2 through 7, which do not possess both chloracetyl and alkoxyalkyl groups on each of the amino groups, do not demonstrate herbicidal or fungicidal activity. For example, Run 2 has a structure very similar to Run 1 with the exception that the 3-amino group does not possess a chloroacetyl group. Run 2 illustrates that herbicidal and fungicidal activity is demonstrated only when both of the amino groups possess a chloroacetyl group and an alkoxyalkyl group.

The compounds of the present invention can be applied in a variety of ways at various concentrations. The desired concentration will vary depending upon the particular compound. However, the desired concentration should be an effective amount taking into account the method of application chosen to deliver these compounds. The effective concentration is easily determined by those skill0d in the art. Methods of delivering the compounds of the present invention include spraying, dusting, drenching and the like.

STATEMENT OF INDUSTRIAL APPLICATION

The invention provides N,N'-bis(alkoxyalkyl)-N,N'-bis(2-haloacetyl)-phenylenediamine compounds which are useful as herbicides and fungicides.

We claim:

1. A compound having the formula:

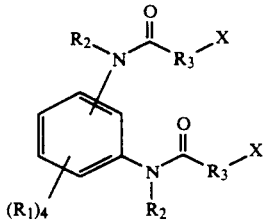

wherein:
each $R_1$ is independently selected from H, a straight chain or branched $C_1$-$C_{10}$ alkyl, $C_1$-$C_8$ alkoxy, $C_2$-$C_{10}$ alkenyl or $C_3$-$C_7$ cycloalkenyl group;
each $R_2$ is independently selected from —$CH_2(CH_2)_mO(CH_2)_nCH_3$ and —$CH(CH_2)_mO(CH_2)_nCH_3$
  |
  $CH_3$ wherein m and n are independently selected integers from 0 to 4, inclusive;
each $R_3$ is independently selected from a straight chain or branched $C_1$-$C_{10}$ alkylene; and
X is independently selected from Cl, Br and I.

2. The compound of claim 1 wherein each $R_1$ is hydrogen.

3. The compound of claim 1 wherein at least one $R_1$ is tert-butyl.

4. The compound of claim 1 wherein $R_3$ is —$CH_2$—.

5. The compound of claim 1 wherein each $R_3$ is —$CH_2CH_2$—.

6. The compound of claim 1 wherein each $R_3$ is —$CH_2CH_2CH_2$—.

7. The compound of claim 1 wherein $R_2$ is —$CH_2(CH_2)_mO(CH_2)_nCH_3$.

8. The compound claim 1 wherein $R_2$ is

—$CH(CH_2)_mO(CH_2)_nCH_3$.
  |
  $CH_3$

9. The compound of claim 1 wherein X is Cl.

10. A compound having the formula:

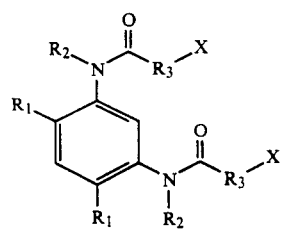

wherein:
each $R_1$ is independently selected from H or a straight chain or branched $C_1$-$C_{10}$ alkyl, $C_1$-$C_8$ alkoxy, $C_2$-$C_{10}$ alkenyl or $C_3$-$C_7$ cycloalkenyl group;
each $R_2$ is independently selected from —$CH_2(CH_2)_mO(CH_2)_nCH_3$ and —$CH(CH_2)_mO(CH_2)_nCH_3$
  |
  $CH_3$ wherein m and n are independently selected integers from 0 to 4, inclusive;
each $R_3$ is independently selected from a straight chain or branched $C_1$-$C_{10}$ alkylene; and
each X is Cl.

11. A compound having the formula:

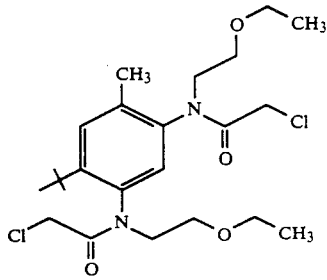

12. A method for controlling weeds and grasses in an agricultural crop which comprises applying to the agricultural crop an effective amount of a compound having the formula:

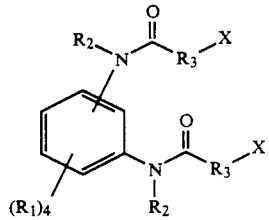

wherein:
each $R_1$ is independently selected from H, a straight chain or branched $C_1$-$C_{10}$ alkyl, $C_1$-$C_8$ alkoxy, $C_2$-$C_{10}$ alkenyl or $C_3$-$C_7$ cycloalkenyl group;
each $R_2$ is independently selected from —$CH_2(CH_2)_mO(CH_2)_nCH_3$ and —$CH(CH_2)_mO(CH_2)_nCH_3$
  |
  $CH_3$ wherein m and n are independently selected integers from 0 to 4, inclusive;
each $R_3$ is independently selected from a straight chain or branched $C_1$-$C_{10}$ alkylene; and
X is independently selected from Cl, Br and I.

13. The method according to claim 12 wherein each $R_1$ is hydrogen.

14. The method according to claim 12 wherein at least one $R_1$ is tert-butyl.

15. The method according to claim 12 wherein $R_3$ is —$CH_2$—.

16. The method according to claim 12 wherein each $R_3$ is —CH$_2$CH$_2$—.

17. The method according to claim 12 wherein each $R_3$ is —CH$_2$CH$_2$CH$_2$—.

18. The method according to claim 12 wherein $R_2$ is —CH$_2$(CH$_2$)$_m$O(CH$_2$)$_n$CH$_3$.

19. The method according to claim 12 wherein $R_2$ is

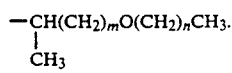

20. The method according to claim 12 wherein X is Cl.

21. A method for controlling weeds and grasses n an agricultural crop which comprises applying to the agricultural crop an effective amount of a compound having the formula:

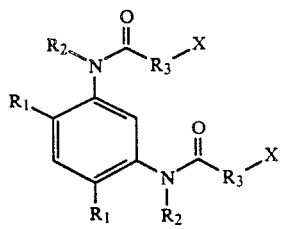

wherein:

each $R_1$ is independently selected from H or a straight chain or branched $C_1$-$C_{10}$ alkyl, $C_1$-$C_8$ alkoxy, $C_2$-$C_{10}$ alkenyl or $C_3$-$C_7$ cycloalkenyl group;

each $R_2$ is independently selected from

—CH$_2$(CH$_2$)$_m$O(CH$_2$)$_n$CH$_3$ and

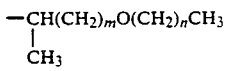

wherein m and n are independently selected integers from 0 to 4, inclusive;

each $R_3$ is independently selected from a straight chain or branched $C_1$-$C_{10}$ alkylene; and each X is Cl.

22. A method for controlling weeds and grasses in an agricultural crop which comprises applying to the agricultural crop an effective amount of a compound having the formula:

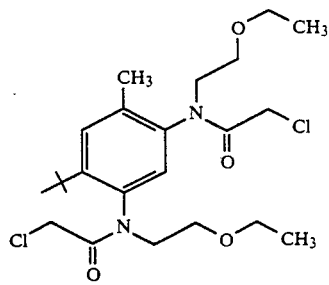

* * * * *